United States Patent [19]

Karra

[11] Patent Number: 5,157,189
[45] Date of Patent: Oct. 20, 1992

[54] CONVERSION OF LIGHT HYDROCARBONS TO HIGHER HYDROCARBONS

[76] Inventor: Sankaram B. Karra, 610 S. Santa Anita Ave., Arcadia, Calif. 91006

[21] Appl. No.: 616,584

[22] Filed: Nov. 21, 1990

Related U.S. Application Data

[63] Continuation-in-part of Ser. No. 110,248, Oct. 19, 1987, Pat. No. 4,973,786.

[51] Int. Cl.$^5$ .............................................. C07C 2/00
[52] U.S. Cl. .................................... 585/500; 585/415; 585/417; 585/654; 585/656; 585/700; 585/943; 585/658
[58] Field of Search ............... 585/415, 417, 500, 654, 585/656, 700, 943, 658

[56] References Cited

U.S. PATENT DOCUMENTS

| | | | |
|---|---|---|---|
| 2,320,274 | 5/1943 | Gorin | 260/673 |
| 2,488,083 | 6/1946 | Gorin | 260/677 |
| 3,014,969 | 12/1961 | Magee | 260/604 |
| 3,448,161 | 6/1969 | Garcia et al. | 260/671 |
| 3,551,506 | 12/1970 | Weinstein | 260/656 |
| 3,848,012 | 11/1974 | Applegath et al. | 260/671 R |
| 3,987,118 | 10/1976 | Kuck | 260/654 A |
| 3,987,119 | 10/1976 | Kurtz et al. | 260/656 R |
| 4,042,639 | 8/1977 | Gordon et al. | 260/656 R |
| 4,199,533 | 4/1980 | Benson | 585/500 |
| 4,465,893 | 8/1984 | Olah | 585/943 |
| 4,467,430 | 8/1984 | Olah | 585/943 |
| 4,543,434 | 9/1985 | Chang | 585/943 |
| 4,544,747 | 10/1985 | Sofranko et al. | 585/500 |
| 4,544,785 | 10/1985 | Withers et al. | 585/943 |
| 4,654,460 | 3/1987 | Kimble et al. | 585/500 |
| 4,695,663 | 9/1987 | Hall | 585/417 |
| 4,714,796 | 12/1987 | Senkan | 585/328 |
| 4,769,504 | 9/1988 | Noceti et al. | 585/415 |
| 4,801,762 | 1/1989 | Leyshon | 585/500 |
| 4,816,286 | 3/1989 | Hirose | 427/39 |
| 4,822,938 | 4/1989 | Audeh et al. | 585/943 |
| 4,879,427 | 11/1989 | Sofranko | 585/943 |

OTHER PUBLICATIONS

Chapter 1, Pyrolysis: Theory & Industrial Practice (Academic Press, 1983) Edited by L. ALbright, B. Crine and W. Corcoran.
Chapter 5, Pyrolysis: Theory & Industrial Practice (Academic Press, 1983), Edited by L. Albright, B. Crine and W. Corcoran.
Chapter 9, Organic Chemistry, (Allyn and Bacon, Inc., 1959, 12th printing, 1965), by Morrison and Boyd.
Lyon, R. K., and Mitchell, J. E., "Modification of Thermal Alkylation with HCl," in Thermal Hydrocarbon Chemistry, American Chemical Society Symposium Series, vol. 183, pp. 289-296 (1979).
"Experimental and Mechanistic Analysis of High Temperature Oxidation of Methane and Chloromethane," doctoral thesis of Sankaram B. Karra (illinois Institute of Technology, 1988).
W. Schreiner et al., "Oxidize HCl for chlorine," *Hydrocarbon Processing* (Nov. 1974).

*Primary Examiner*—Patrick P. Garvin
*Assistant Examiner*—E. D. Irzinski
*Attorney, Agent, or Firm*—McDermott, WIll & Emery

[57] ABSTRACT

A process is disclosed for catalytically converting light hydrocarbons, such as natural gas, to saturated or unsaturated higher molecular weight hydrocarbons, such as ethylene, propylene, ethyl benzene, and styrene. The process employs gaseous catalyst or a mixture of catalysts selected from hydrogen sulfide, hydrogen halides other then hydrogen fluoride, halogen other than fluorine, sulfur vapor, and/or sulfur containing hydrocarbons.

19 Claims, No Drawings

CONVERSION OF LIGHT HYDROCARBONS TO HIGHER HYDROCARBONS

This application is a continuation-in-part of my co-pending Ser. No. 07/110,248, filed Oct. 19, 1987, and now U.S. Pat. No. 4,973,786, which is incorporated herein by reference and made a part hereof.

FIELD OF THE INVENTION

This invention relates to the field of light hydrocarbon conversion to higher molecular weight hydrocarbons and synthesis gas and, in particular, the homogeneous catalytic conversion of methane and methane-containing hydrocarbons to higher molecular weight saturated and unsaturated hydrocarbons and synthesis gas.

BACKGROUND OF THE INVENTION

Methane is abundantly available in nature in the form of natural gas, which typically contains about 75% methane by weight. Methane is also produced by other means, such as anaerobic biological processes. Although methane is primarily used as fuel, it is also a valuable starting material for the production of synthesis gas and a number of important higher molecular weight saturated and unsaturated hydrocarbons, such as ethane, ethylene, propylene, acetylene and benzene. These compounds, in turn, are useful starting materials in the production of other commercially important petrochemicals and polymers.

Processes are known for converting methane into higher molecular weight hydrocarbons, including aliphatic and aromatic hydrocarbons, using a technique known as "pyrolysis." Such processes use heat to accomplish pyrolysis chemical reactions without the presence of substantial amounts of free oxygen or oxygen containing gas. Furthermore, diamond films can be synthesized onto solid substrates by pyrolyzing methane in the presence of hydrogen on the heated solid substrate. A general discussion of the high temperature pyrolysis of methane can be found, for example, in chapter 1 of *Pyrolysis: Theory and Industrial Practice* (Academic Press, 1983), edited by L. Albright, B. Crynes, and W. Corcoran, which is incorporated herein by reference and made a part hereof.

Methane can be converted into higher molecular weight hydrocarbons by a number of other processes which also involve the use of pyrolysis. For example, U.S. Pat. No. 2,488,083 to Gorin describes a process for converting methane into normally liquid hydrocarbons by first converting it into methyl halide and then pyrolytically condensing methyl halide into the desired end products. In this process, lower pyrolysis temperatures are made possible by the use of metal based alumina silica catalysts. Benson U.S. Pat. No. 4,199,533 describes a method for producing higher molecular weight hydrocarbons by reacting methane and chlorine. U.S. Pat. No. 4,714,796 to Senkan describes a two-step process in which methane is first converted into methyl halides, which are then pyrolyzed in the presence of oxygen to obtain higher molecular weight hydrocarbons. U.S. Pat. No. 4,544,747 to Sofranko et al. also describes a process of methane conversion using reducible solid metal oxide catalysts with a halogen promotor. U.S. Pat. No. 4,654,460 to Kimble et al. describes a process for oxidative conversion of methane using a solid contact material comprised of various metals, phosphate radicals, and, optionally, halogen ions and halogen ion containing compounds as promoters. U.S. Pat. No. 4,769,504 to Noceti et al. describes a two-step process for the production of gasoline range hydrocarbons from lower alkanes.

U.S. Pat. No. 4,513,164 to Olah describes a process for methane conversion into gasoline range isoalkane mixtures, cycloalkanes and aromatics containing less than 12 carbon atoms, but no olefins, using superacidic heterogeneous catalysts. This patent also describes a two-step process for selectively converting methane into monosubstituted derivatives using halogens and sulfur by superacidic ionic reaction catalysts and further condensation of monosubstituted derivatives into gasoline range hydrocarbon mixtures but no olefins. It is known that such Friedel-Crafts ionic alkylation processes proceed through ionic reactions rather than free radical reaction pathways resulting in the formation of higher molecular weight normal and isoalkanes.

Processes are also known for converting methane into so-called "synthesis gas", a mixture of carbon monoxide (CO) and hydrogen ($H_2$) using metal-based heterogeneous catalysts. Synthesis gas can be catalytically converted into formaldehyde, methanol, and other useful hydrocarbons in accordance with known processes.

Methane can also be converted into benzene and other aromatic hydrocarbons by first converting it into methyl halide and then pyrolyzing the resulting methyl halide using solid metal oxide catalysts. Such a process is described, for example, in U.S. Pat. No. 2,320,274 to Gorin. U.S. Pat. No. 4,695,663 to Hall et al. describes a process for converting methane-containing hydrocarbons into aromatics in the absence of oxygen using solid aluminosilicate catalyst.

None of the methane conversion processes described above can be used for simultaneously producing both higher molecular weight hydrocarbons and synthesis gas. The advantages of direct natural ga conversion into such products at the well site are significant, because the resulting products are less expensive and less dangerous to transport than natural gas.

In my co-pending application Ser. No. 07/110,248, I described a direct conversion process for simultaneously producing synthesis gas and higher molecular weight hydrocarbons from methane and other hydrocarbons.

Processes are also known for producing higher molecular weight hydrocarbons, such as aromatic and alkyl aromatic hydrocarbons, via Diels-Alder cyclization reactions of lower olefinic and acetylinic hydrocarbons, such as acetylene, vinyl acetylene, butadiene etc. Such cyclization reaction Processes are summarized in chapter 5 of *Pyrolysis: Theory and Industrial Practice* (Academic Press, 1983), edited by L. Albright, B. Crynes, and W. Corcoran, which is incorporated herein by reference and made a part hereof. The processes of coal liquefaction and gassification is another major source for aromatics.

Processes for producing alkyl benzenes and styrene are also known. In most of these processes, the starting material is benzene or toluene. Ethyl benzene is produced by Friedel-Crafts alkylation of benzene and ethylene using a variety of heterogeneous catalysts and promoters. Styrene monomer is produced by dehydrogenation of ethyl benzene. A general discussion of Friedel-Crafts alkylation and pyrolytic dehydrogenation can be found in chapter 9 of *Organic Chemistry* (Allyn and Bacon, Inc., 1959, 12th printing, 1965) by Morrison and Boyd, which is incorporated herein by reference and made a part hereof.

U.S. Pat. No. 3,848,012 to Applegath et al. describes a process for continuously producing ethyl benzene by reaction of benzene and ethylene in the liquid phase using small amounts of aluminum chloride as Friedel-Crafts alkylation catalyst. U.S. Pat. No. 3,448,161 to Garcia et al. also describes an alkylation process for producing ethyl benzene by reacting benzene and ethylene and an aluminum chloride catalyst complex.

Simultaneous reactions of natural gas (which comprises a mixture of methane, ethane, and small amounts of propane and other higher normal alkanes) and higher molecular weight products of natural gas conversion processes (such as higher olefins and aromatic hydrocarbons) to produce valuable chemicals, such as ethylene and other olefins, ethyl benzene, xylenes, styrene monomer, etc., would also be desirable, since they provide a potential route for better methane and ethane utilization. Such utilization of natural gas by simultaneously reacting it with methyl or ethyl group containing higher molecular weight hydrocarbons to produce corresponding higher alkanes and olefins would be of further value. By this route, paraffinic, naphthenic and aromatic hydrocarbons produced by direct natural gas conversion processes could be further converted into more useful products by pyrolytic oxidation.

SUMMARY OF THE INVENTION

The present invention provides a process for direct conversion of gaseous hydrocarbons, such as methane-containing hydrocarbons like natural gas, into synthesis gas (carbon monoxide and hydrogen) and one or more saturated or unsaturated higher molecular weight hydrocarbons.

The invention employs a homogeneous catalyst or mixture of catalysts selected from the hydrogen halides (other than hydrogen fluoride), hydrogen sulfide, halogens other than fluorine, and sulfur vapor to facilitate pyrolytic oxidation reactions of methane with free oxygen or free oxygen containing gas under conditions of elevated temperature.

More specifically, one embodiment of the invention provides a process for preparing synthesis gas (carbon monoxide and hydrogen) and one or more saturated or unsaturated higher molecular weight hydrocarbons. The process comprises reacting methane-containing hydrocarbons, such as natural gas, and free oxygen or free oxygen containing gas in the presence of a gaseous hydrogen sulfide catalyst under conditions that permit the pyrolytic oxidation of methane with substantial regeneration of hydrogen sulfide Sulfur vapor may be used to provide a source of hydrogen sulfide.

Another embodiment of the invention comprises reacting methane-containing hydrocarbons, such as natural gas, and free oxygen or free oxygen containing gas in the presence of a gaseous halogen catalyst other than fluorine under conditions that permit the pyrolytic oxidation of methane and the formation of hydrogen halide. Hydrogen halide can, in turn, be recycled for use as a catalyst or converted back into halogen.

An alternative embodiment of the invention comprises reacting methane, one or more compounds selected from the group consisting of benzene and the alkyl benzenes, and free oxygen in the presence of a homogeneous gas-phase catalyst under conditions that permit pyrolytic oxidation of methane. This catalyst comprises one or more compounds selected from the group consisting of gaseous hydrogen halide other than hydrogen fluoride, hydrogen sulfide, gaseous halogen other than fluorine, and sulfur vapor. The products of this process include aromatic hydrocarbons containing alkyl and/or vinyl substituents, saturated or unsaturated aliphatic hydrocarbons, and synthesis gas (carbon monoxide and hydrogen).

The process is a single stage conversion process and can be operated so as to produce a desired mix of the products. It is simple, economical, and can be readily used at the natural gas well site. In addition, the process operates without substantial formation of undesirable by-products, such as solid graphite or soot. Finally, the process operates without production of a destructive flame, in which substantial amounts of carbon dioxide ($CO_2$) are produced.

The synthesis gas produced by the process can be used to manufacture a variety of chemicals, such as alcohols, ethers and higher hydrocarbons. In addition, the process can be operated at lower pyrolytic temperatures (between about 500° C. and about 1000° C. and, in some instances, between about 400° C. and about 1100° C.) and at any desirable pressure. Therefore, at a given pressure, use of the process results in substantial savings over existing processes.

DETAILED DESCRIPTION

In the process of the present invention, gaseous hydrocarbons, including methane-containing hydrocarbons like natural gas (which comprises a mixture of methane, ethane, and small amounts propane and other higher alkanes), free oxygen or free oxygen containing gas and homogeneous catalyst are combined in a reactor in the desired molar ratios. In general, the catalyst can be any one or more compounds selected from (a) hydrogen halides other than hydrogen fluoride, (b) hydrogen sulfide, (c) halogen other than fluorine, and (d) sulfur vapor.

As primary reactant in this process, one can use methane alone or methane-containing hydrocarbons, such as natural gas. When natural gas is used, the high molecular weight components of the natural gas can be regarded as excess hydrocarbons. Free oxygen containing gas, such as air, can be used as the source of oxygen. It is preferred that the reactants be present in the following molar ratios: methane to oxygen, between about 10:1 and about 1:1, and methane to catalyst, between about 20:1 and about 1:1.

Pyrolytic oxidation takes place under the same conditions used for the pyrolysis of methane or methyl chloride without the presence of substantial amounts of free oxygen. These conditions are described in greater detail in the treatise Pyrolysis: Theory and Industrial Practice, which is cited above and incorporated herein by reference, and in my copending patent application Ser. No. 07/110,248, filed Oct. 19, 1987, which is also incorporated herein by reference. The temperature of pyrolytic oxidation is preferably maintained at above 500° C. and, more particularly, between about 500° C. and about 1000° C. In some instances, temperatures between about 400° C. and 1100° C. may be used. The reaction is maintained at a desirable pressure, preferably atmospheric pressure, by withdrawing products at an appropriate rate. The time for the reaction depends on the operating conditions, the desired degree of conversion, and desired product ratios. Typically, however, the time needed is in the order of seconds.

In one embodiment of the invention, gaseous hydrogen sulfide is employed as homogeneous gas-phase catalyst. The hydrogen sulfide catalyst is substantially regenerated during the course of the reaction and can be recycled for reuse. Sulfur vapor, which generates hydrogen sulfide during the reaction, may be used as a source of hydrogen sulfide catalyst. (See Equations (8) to (10) below.) Pyrolytic oxidation takes place under the same conditions set forth above.

The products of the reaction are quenched from reacting further and separated into various desirable components or mixtures of components using known separation techniques. After separation of the various products, the excess unreacted reactant hydrocarbons and some products may be recycled to the reaction chamber. The catalysts are substantially regenerated and can be reused.

The overall reactions believed to be taking place within the reaction chamber, which are more fully described below, can be represented by equilibria reactions. Accordingly, the composition of the resultant products can be controlled by varying the ratios of reactants, the temperature, and/or the pressure within the reactor, use of diluents such as nitrogen and water vapor, and recycling unreacted reactant hydrocarbons and some products, as is well known in the art.

It is believed that a number of reactions take place in the reactor. One such reaction produces carbon monoxide and hydrogen. When the catalyst includes hydrogen sulfide or hydrogen halide, the reaction proceeds according to the following thermodynamically favorable equations:

(1) $CH_4 + O_2 + H_2S \rightleftharpoons CO + H_2 + 2H_2O + 1/n\ S_n$
(2) $CH_4 + O_2 + 2HX \rightleftharpoons CO + H_2 + 2H_2O + X_2$, where n is the number of S atoms in polynuclear sulfur. The hydrogen halide component of the catalyst is represented by HX, where X is a halide other than fluorine.

Other thermodynamically favorable reactions produce the higher molecular weight hydrocarbons. When hydrogen sulfide is used as catalyst, the following reactions are believed to occur:

(3) $2CH_4 + O_2 + H_2S \rightleftharpoons C_2H_{6-m} + m/2\ H_2 + 2H_2O + 1/n\ S_n$, (m=0,2,4,)
(4) $3CH_4 + O_2 + H_2S \rightleftharpoons C_3H_{8-m} + m/2\ H_2 + 2H_2O + 1/n\ S_n$ (m=0,2,4)
(5) $4CH_4 + O_2 + H_2S \rightleftharpoons C_4H_{10-m} + m/2\ H_2 + 2H_2O + 1/n\ S_n$ (m=0,2,4,6)
(6) $6CH_4 + O_2 + H_2S \rightleftharpoons C_6H_6 + 8H_2 + 2H_2O + 1/n\ S_n$
(7) $5CH_4 + C_2H_6 + O_2 + H_2S \rightleftharpoons C_6H_5CH_3 + 8H_2 + 2H_2O + 1/n\ S_n$ Alternatively, when hydrogen halides are used, reactions analogous to those set forth above produce higher molecular weight hydrocarbons and liberate halogen molecule. During the progress of the above reactions, oxides of sulfur and halogen, such as sulfur dioxide, can form as intermediates which can also serve as oxidants. Halogenated hydrocarbons, such as haloethanes and vinyl halides, can also form during the progress of these reactions.

The halogen gas and/or sulfur vapor produced during the progress of these reactions further reacts with methane and oxygen whereby carbon monoxide, hydrogen, and various higher molecular weight hydrocarbons are produced. (See Equations (8) to (10) below.) In this fashion, hydrogen halide and/or hydrogen sulfide catalyst is regenerated and can be recycled for reuse.

In another embodiment of the present invention, halogen other than fluorine and/or sulfur vapor are used as catalysts, resulting in the formation of hydrogen halide and/or hydrogen sulfide, respectively. Hydrogen halide and hydrogen sulfide can, in turn, be recycled for reuse as catalysts (see Equations 1-7 above) or converted into halogen or sulfur vapor, respectively (see Equations 19-24 below), and then reused. Thus, compounds useful as catalysts are generated during the course of the reaction. In this embodiment, the preferred halogen catalyst is bromine and the reactants are preferably present in the following molar ratios: methane to oxygen, between about 10:1 and about 1:1, and methane to halogen and/or sulfur, between about 10:1 and about 1:1.

It is believed that production of synthesis gas and $C_2$ hydrocarbons by the use of halogen and/or sulfur vapor occurs according to the thermodynamically favorable reactions of the type:

(8) $CH_4 + \frac{1}{2}O_2 + 1/n\ S_n$ (or $X_2$) $\rightleftharpoons CO + H_2O + H_2S$ (or 2HX)
(9) $2CH_4 + \frac{1}{2}O_2 + 1/n\ S_n$ (or $X_2$) $\rightleftharpoons C_2H_4 + H_2O + H_2S$ (or 2HX)
(10) $2CH_4 + 1/n\ S_n$ (or $X_2$) $\rightleftharpoons C_2H_{6-m} + m/2\ H_2 + H_2S$ (or 2HX) (m=0,2,4), where X is halogen other than fluorine and n is the number of atoms in polynuclear sulfur. In a similar fashion, $C_3$, $C_4$, $C_6$ and higher hydrocarbons are also produced. It will be understood from Equations (8) to (10) above that sulfur vapor can provide a source of hydrogen sulfide catalyst which can be used in the processes of the present invention, and halogen (represented by general formula $X_2$, where $X_2$ is halogen molecule other than fluorine) can provide a source of hydrogen halide catalyst. This is due to the fact that hydrogen sulfide and hydrogen halide, respectively, are formed from these starting materials during the course of pyrolytic oxidation. It will also be understood that hydrocarbons having easily abstractable halogen or sulfur, such as chloro or bromomethane, dimethyl sulfide, and methyl mercaptan, can also be used as a source of halogen and sulfur in the process of the present invention.

In an alternative embodiment of the present invention, methane-containing hydrocarbons like natural gas, aromatic hydrocarbons such as benzene or alkyl benzenes, free oxygen or free oxygen containing gas, and catalyst(s) are combined in a reactor in the desired molar ratios. Any of the foregoing catalysts may be used, including one or more compounds selected from (a) hydrogen halides other than hydrogen fluoride, (b) hydrogen sulfide, (c) halogen other than fluorine, and (d) sulfur vapor. Preferably, the reactants are present in the following molar ratios: methane to oxygen, between about 10:1 and about 1:1, methane to catalyst, between about 10:1 and about 1:1, and methane to aromatics, about 1:1 or methane in excess. Reaction takes place under the same conditions set forth above. In addition to the reactions described so far, when these reactants are used several other reactions are believed to take place. These additional reactions are believed to cause the formation of variety of aromatic hydrocarbons containing alkyl and/or vinyl substituents (i.e., alkyl aromatics and corresponding olefinic aromatics), including styrene monomer and vinyl toluene. When hydrogen halides are used as catalyst, it is believed that the following reactions occur:

(11) $CH_4 + RH + 2HX + O_2 \rightleftharpoons RCH_3 + 2H_2O + X_2$

(12) $CH_4 + RH + 2HX + O_2 \rightleftharpoons R' = CH_2 + H_2 + 2H_2O + X_2$

(13) $C_2H_6 + RH + 2HX + O_2 \rightleftharpoons RC_2H_5 + 2H_2O + X_2$

(14) $C_2H_6 + RH + 2HX + O_2 \rightleftharpoons RCH = CH_2 + H_2 + 2H_2O + X_2$

(15) $CH_4 + RCH_3 + 2HX + O_2 \rightleftharpoons RCH = CH_2 + H_2 + 2H_2O + X_2$

(16) $CH_4 + RCH_3 + 2HX + O_2 \rightleftharpoons R'(CH_3)_2 + 2H_2O + X_2$

(17) $CH_4 + ROH + 2HX \rightleftharpoons RCH_3 + H_2 + H_2O + X_2$

(18) $CH_4 + ROH + 2HX \rightleftharpoons R' = CH_2 + 2H_2 + H_2O + X_2$, where R can be an aliphatic or aromatic hydrocarbon group and can also contain halogen, sulfur and/or oxygen atom, and where R' is the group R with one less hydrogen atom. Preferably, R is one or more of the following aliphatic or aromatic groups: butadienyl, cyclohexanyl, phenyl, or benzyl. Hydrogen halide other than hydrogen fluoride is represented by HX. The halogen component of the catalyst is represented by $X_2$, where $X_2$ is a halogen molecule other than fluorine. Similarly, hydrogen sulfide or other sulfur containing compounds (e.g., methyl mercaptan and dimethyl sulfide) and halogen containing compounds (e.g., chloro or bromomethane) can also be used as catalysts.

The halogen gas and/or sulfur vapor produced during the progress of these reactions further reacts with the normally gaseous hydrocarbons (such as methane) and/or aromatics in the presence of free oxygen and/or free oxygen containing gas, whereby alkyl aromatics, corresponding olefinic aromatics, as well as saturated or unsaturated aliphatic hydrocarbons are produced with substantial regeneration of hydrogen halide and/or hydrogen sulfide. In this fashion, the hydrogen halide and/or hydrogen sulfide catalyst is regenerated and can be recycled for reuse.

An important feature of this process from a practical standpoint is that exothermic or substantially thermoneutral reactions are involved. Destructive flames in the reactor can easily be avoided by proper control of specific temperatures for the reaction, by selecting optimum operational reactant composition, and by using nitrogen, water vapor and/or carbon dioxide as diluent. In this regard, it is well known that the hydrogen halides and halogens, and in particular hydrogen bromide and bromine, are superior flame retardants.

Hydrogen halide and/or hydrogen sulfide catalysts are separated from the products by means well known in the art and can be recycled. Examples of processes used to accomplish such separations are numerous. Schreiner et al., "Hydrocarbon Processing," November 1974, pp. 151-56, which is incorporated herein by reference and made a part hereof, discusses a process for producing $Cl_2$ by HCl oxidation. Likewise, U.S. Pat. No. 4,959,202 to Minet et al., which is also incorporated herein by reference and made a part hereof, describes a process for recovery of chlorine from hydrogen chloride by a carrier catalyst process. Complete separation of water vapor is not needed, since steam can be recycled as diluent. When hydrogen halide and/or hydrogen sulfide are used as catalysts, a convenient way of producing halogen and/or sulfur is in accordance with the following equations:

(19) $4HX + O_2 \rightleftharpoons 2X_2 + 2H_2O$

(20) $2H_2S + O_2 \rightleftharpoons 2/n\ S_n + 2H_2O$, where X is halogen other than fluorine and n is the number of atoms in polynuclear sulfur. During the progress of the above reactions, depending on the temperature level of the reaction system, oxides of sulfur and halogen may form as intermediates which can also serve as oxidants in this process.

Halogen gas other than fluorine and/or sulfur vapor can also be produced by coupled reactions between hydrogen halides, hydrogen sulfide, and oxides of sulfur, nitrogen, halogens and carbon. It is believed this occurs according to the following chemical equations:

(21) $2HX + H_2S + SO_2 \rightleftharpoons X_2 + 2/n\ S_n + 2H_2O$

(22) $2HX + H_2S + CO + \frac{1}{2}O_2 \rightleftharpoons X_2 + 1/n\ S_n + 2H_2 + CO_2$

(23) $2HX + SO_2 + CO \rightleftharpoons X_2 + 1/n\ S_n + H_2O + CO_2$

(24) $2HX + H_2S + 2NO \rightleftharpoons X_2 + 1/n\ S_n + N_2 + 2H_2O$, where $S_n$ is polynuclear sulfur. During the progress of the above reactions, sulfur halides, oxygenated sulfur halides, halogen, and sulfur containing oxides of carbon and nitrogen can form, which can also serve as sources of halogen and sulfur in the process.

It is to be noted that the equilibria reactions described above are combined equilibria representing several free radical and molecular reactions proceeding at a particular rate in the pyrolytic oxidation process. Illustration of the invention may be possible by simulation of the progress rates of the reactions in the process. For the purpose of illustrating the invention, the following examples are given:

EXAMPLE 1

Methane is reacted with oxygen in air in the presence of hydrogen sulfide at a temperature of about 850° C. The molar ratios of the reaction mixture are as follows: methane to hydrogen sulfide, about 3.0:1, and methane to oxygen in air, about 2.5:1. The reaction proceeds to yield products until between 40% and 50% of the methane is converted. The catalyst hydrogen sulfide remains substantially unchanged. The product mixture constitutes primarily carbon monoxide, hydrogen, ethylene, propylene, acetylene, water vapor, excess unreacted methane, and small amounts of higher homologues and oxygenated derivatives. The major products are carbon monoxide, hydrogen, and water vapor. However, there are significant yields of ethylene and acetylene.

EXAMPLE 2

The procedure of Example 1 is followed at a temperature of 800° C., except that an additional catalyst, bromine, is added which results in the following molar ratios of reactants: methane to hydrogen sulfide, about 3.0:1, methane to oxygen in air, about 4.5:1, and methane to bromine, about 3.0:1. The reaction proceeds to yield products until between 40% and 50% of the methane is converted. The primary products are similar to those in Example 1. The sum of the yields of ethylene and acetylene and the yields of carbon monoxide and hydrogen are at similar and significant levels.

EXAMPLE 3

Methane is reacted with oxygen in air in the presence of chlorine at a temperature of about 850° C. The molar ratios of the reaction mixture are as follows: methane to oxygen in air, about 5.0:1 and methane to chlorine, about 2.5:1. About 25 mole percent of steam is used as diluent. The reaction proceeds to yield products until between 40% and 60% of the methane is converted. The product mixture constitutes primarily carbon monoxide, hydrogen, ethylene, propylene, acetylene, water vapor, excess unreacted methane, small amounts of higher homologues and oxygenated derivatives and hydrogen chloride. Significant yields of ethylene and acetylene are obtained.

EXAMPLE 4

Methane, ethane and toluene are reacted with oxygen in air in the presence of hydrogen iodide and chlorine at a temperature of about 800° C. The molar ratios of reactants are as follows: methane to ethane, about 5:1, methane to toluene, about 1:1, methane to hydrogen iodide, about 3.0:1, methane to oxygen in air, about 5.0:1 and methane to chlorine, about 5.0:1. About 10 mole percent of steam is used as diluent. The reaction proceeds to yield products until between 30% and 60% of the methane and toluene are converted. The primary products are carbon monoxide, hydrogen, ethylene, acetylene, styrene monomer, water vapor, and small amounts of higher homologues. The sum of the yields of ethylene, acetylene and styrene, and the yields of carbon monoxide and hydrogen are at similar and significant levels.

EXAMPLE 5

Ethane and toluene are reacted with oxygen in the presence of chloro or bromomethane and methyl mercaptan at a temperature of about 700° C. The molar ratios of the reaction mixture are as follows: ethane to oxygen, about 10:1, ethane to toluene, about 1:1, ethane to chloro or bromomethane about 10:1, ethane to methyl mercaptan, about 5:1. About 20 mole percent of steam is used as diluent. The reaction proceeds to yield products until between 50% and 60% of the ethane and toluene are converted. The product mixture constitutes primarily hydrogen, ethyl benzene, xylene, styrene monomer, ethylene, acetylene, excess unreacted ethane and toluene, small amounts higher homologues, hydrogen sulfide, hydrogen bromide, and hydrogen chloride. Significant yields of styrene monomer, ethylene and acetylene are obtained.

The invention has been described with particular reference to the conversion of natural gas, and natural gas and alkyl benzenes to corresponding olefinic and acetylinic compounds. However, it is to be understood that the invention is applicable to co-pyrolytic oxidation of other hydrocarbons containing methyl and/or ethyl group into corresponding olefinic, acetylinic, naphthenic, and aromatic hydrocarbons. It is also to be understood that other hydrogenated species containing mobile hydrogen, mobile halogen and/or mobile sulfur, such as halomethanes, methyl mercaptan, and dimethyl sulfide can also be used as a substitute for halide and sulfide catalysts.

Furthermore, the presence of oxygen atoms in these halide or sulfide catalysts or use of oxides of nitrogen and sulfur reduces the amount of oxygen requirement for the pyrolytic oxidation. In addition, although the invention has been described with particular reference to homogeneous phase catalysts, it will be understood that solid metal oxide catalysts such as silica or alumina, aluminosilicates, transition metals on suitable supports, metal halides, and metal sulfides may be used in combination with homogeneous phase catalysts described herein to reduce the temperatures required for pyrolytic oxidation. At higher temperatures, however, metal carbides can form as byproducts. Use of such solid catalysts in addition to the homogeneous phase catalysts described herein also results in the production of significant yields of oxygenated derivatives, such as formaldehyde and methanol, dimethyl ether and halogen and/or sulfur containing hydrocarbons. It is also to be understood that the catalysts described in the invention can also be used in the other pyrolytic processes, such as conversion of isobutane to isobutylene, production of methyl tertiary butyl ether and conversion of hydrohalosilanes to higher silicones.

I claim:

1. A process for preparing carbon monoxide, hydrogen, and one or more saturated or unsaturated higher molecular weight hydrocarbons which comprises: reacting methane and free oxygen in the presence of a gaseous hydrogen sulfide catalyst under conditions that permit pyrolytic oxidation of methane and substantial regeneration of said gaseous catalyst.

2. The process of claim 1 in which a source of methane is methane-containing hydrocarbons.

3. The process of claim 2 in which a source of methane is natural gas.

4. The process of claim 1 in which a source of free oxygen is a free oxygen containing gas.

5. The process of claim 4 in which the free oxygen containing gas is air.

6. The process of claim 1 in which a source of hydrogen sulfide catalyst is sulfur vapor.

7. A process for preparing carbon monoxide, hydrogen, and one or more saturated or unsaturated higher molecular weight hydrocarbons which comprises: reacting methane and free oxygen in the presence of a gaseous halogen other than fluorine under conditions that permit pyrolytic oxidation of methane and formation of hydrogen halide.

8. The process of claim 7 in which a source of methane is methane-containing hydrocarbons.

9. The process of claim 8 in which a source of methane is natural gas.

10. The process of claim 7 in which a source of free oxygen is a free oxygen containing gas.

11. The process of claim 10 in which the free oxygen containing gas is air.

12. A process for preparing aromatic hydrocarbons containing alkyl and/or vinyl substituent groups, saturated or unsaturated aliphatic hydrocarbons, carbon monoxide, and hydrogen which comprises simultaneously reacting methane, one or more compounds selected from the group consisting of benzene and the alkyl benzenes, and free oxygen in the presence of a homogeneous gas-phase catalyst which comprises one or more compounds selected from the group consisting of hydrogen sulfide and sulfur vapor under conditions that permit pyrolytic oxidation of methane and formation of hydrogen sulfide.

13. The process of claim 12 in which a source of methane is methane-containing hydrocarbons.

14. The process of claim 13 in which a source of methane is natural gas.

15. The process of claim 14 in which a source of free oxygen is a free oxygen containing gas.

16. The process of claim 15 in which the free oxygen containing gas is air.

17. The process of claim 6 in which a source of methane is methane-containing hydrocarbons.

18. The process of claim 6 in which a source of free oxygen is a free oxygen containing gas.

19. The process of claim 9 in which the saturated and unsaturated hydrocarbons include halogenated hydrocarbons having two or more carbon atoms.

* * * * *